United States Patent
Kopelman

(10) Patent No.: US 7,247,493 B2
(45) Date of Patent: Jul. 24, 2007

(54) REUSABLE PH SENSOR DEVICE AND RELATED METHODS

(75) Inventor: Roni Aron Kopelman, Seattle, WA (US)

(73) Assignee: Virbac Corporation, Fort Worth, TX (US)

( * ) Notice: Subject to any disclaimer, the term of this patent is extended or adjusted under 35 U.S.C. 154(b) by 0 days.

(21) Appl. No.: 11/127,849

(22) Filed: May 12, 2005

(65) Prior Publication Data

US 2005/0265895 A1 Dec. 1, 2005

Related U.S. Application Data

(60) Provisional application No. 60/610,886, filed on Sep. 17, 2004, provisional application No. 60/571,905, filed on May 18, 2004.

(51) Int. Cl.
G01N 21/00 (2006.01)
G01N 21/01 (2006.01)
G01N 21/63 (2006.01)
G01N 21/64 (2006.01)
G01N 31/16 (2006.01)
G01N 31/22 (2006.01)
G01N 33/50 (2006.01)
B32B 5/02 (2006.01)
B32B 27/04 (2006.01)
B32B 27/12 (2006.01)

(52) U.S. Cl. ............... 436/163; 436/68; 422/57; 422/82.06; 422/82.07; D10/81

(58) Field of Classification Search ............ 436/163, 436/68; 422/57, 82.07, 82.06; D10/81
See application file for complete search history.

(56) References Cited

U.S. PATENT DOCUMENTS

| 3,176,577 | A | * | 4/1965 | Frank | 356/412 |
| D216,258 | S | * | 12/1969 | Connolly | D10/81 |
| 3,501,852 | A | * | 3/1970 | Hartel et al. | 434/98 |
| 5,217,444 | A | * | 6/1993 | Schoenfeld | 604/361 |
| 6,379,969 | B1 | * | 4/2002 | Mauze et al. | 436/68 |
| 6,562,297 | B1 | * | 5/2003 | Bonstein et al. | 422/56 |
| 2003/0211011 | A1 | | 11/2003 | Phillips et al. | |

* cited by examiner

Primary Examiner—Jill Warden
Assistant Examiner—Keri Moss
(74) Attorney, Agent, or Firm—Bracewell & Giuliani LLP

(57) ABSTRACT

The present invention relates to devices, methods, and kits for quickly and easily measuring and monitoring the pH of aquatic environments, such as lakes, streams, drinking waters, fisheries, aquariums, pools, hot-tubs, and spas. The current invention includes devices that are reusable and capable of monitoring the pH in a reversible fashion, thereby allowing continuous pH sensing without a need for the user to physically perform pH tests. Operation of the invention involves placing the device into the aquatic environment and optically detecting a color change in the membrane, for example, by looking at the device, when a pH measurement is desired. In addition, the device is both inexpensive and reusable, allowing the user to monitor the pH of various aquatic environment at minimal costs.

38 Claims, 4 Drawing Sheets

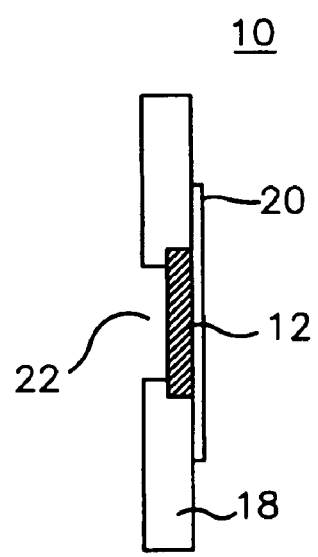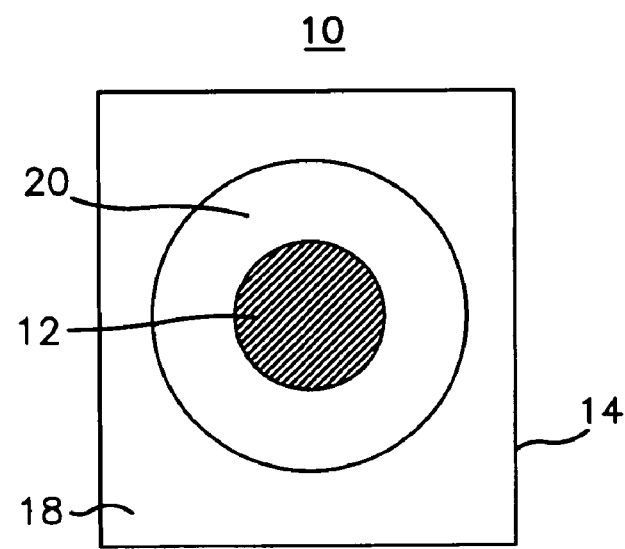
FIG. 2A  FIG. 2B

REUSABLE PH SENSOR DEVICE AND RELATED METHODS

CROSS REFERENCE TO RELATED APPLICATIONS

The application claims the benefit of priority under 35 U.S.C. § 119(e) of U.S. Ser. No. 60/571,905, filed on May 18, 2004, and U.S. Ser. No. 60/610,886, filed on Sep. 17, 2004, the entire content of each of which is incorporated herein by reference.

BACKGROUND OF THE INVENTION

1. Field of the Invention

The invention relates generally to monitoring aspects of water chemistry and more specifically to methods and reusable devices for detecting and continuously monitoring pH of aquatic environments.

2. Background Information

The balance of various chemical components or parameters in an aquatic environment is generally referred to as "water chemistry". Water chemistry is highly determinative of the health and safety of an aquatic environment and the suitability of water for various uses. In many aquatic environments such as fisheries, lakes, drinking water, including recreational waters such as pools, spas, and hot tubs, maintenance of conditions suitable for use, potability, healthy bathing, etc., as well as an aesthetically pleasing environment, is highly dependent on a proper balance of water chemistry parameters. Maintaining a proper water chemistry balance requires constant monitoring and is necessary in preventing the unwanted effects of altered water chemistry, such as skin and eye irritation of bathers, cloudy water, staining and corrosion of pool equipment, and formation of unsightly mineral deposits. Additionally, monitoring and maintaining proper water chemistry in drinking water or environments containing aquatic life (e.g., fish), such as fisheries or aquariums, is vital to ensuring conditions that ensure a healthy water supply, as well as ensure the health and survival of the aquatic life present. For example, altered levels of ammonia or nitrogen, or incorrect pH levels can result in discolored water, algae blooms, outbreak of disease, and fish loss. As such, accurately determining various aspects of water chemistry is of critical importance for determining the suitability of water for various applications, as well as maintaining the health and safety of a water sample.

Water pH is one of the most important parameters of water chemistry. The pH scale is a measure of the acidity or amount of free hydrogen ions in the water. The pH scale extends from 0 to 14, with a pH value of 7.0 corresponding to a neutral pH. As the pH moves lower than 7.0, the water becomes increasingly acidic, and as the pH moves higher than 7.0, the water becomes less acidic and more basic. Because pH is measured with a logarithmic scale, very small changes in the value indicate large changes in hydrogen ion concentration. For example, a change of one pH unit corresponds to a ten fold difference in the number of free hydrogen ions. The pH value of aquatic environments such as aquariums, pools, and spas is vital not only because it is itself an important parameter, but also because other water chemistry parameters (e.g., ammonia, total alkalinity, chlorine, and phosphates) are dependent on the pH value. Because of the importance of this parameter, the pH of aquariums, pools, and hot-tubs must be monitored frequently to adjust accordingly to small changes in the pH values.

Several methods are currently used to test the pH value of aquatic environments. Perhaps the most common method is a method utilizing solutions containing indicator dyes, which change color corresponding to the pH of the water sample. Such methods include removing a small sample of water from the aquatic environment and adding a dye solution calibrated to test the pH. The combination of the dye solution and the water sample is allowed to develop a color, and the color of the water-dye mix is compared to reference colors corresponding to pH values. The solutions are then discarded following comparison of the water-dye mix to reference colors and determining the pH of the sample. This method is inexpensive, making it popular for residential applications, but is time consuming and user-intensive. The user must first remember to check the pH, and then perform several physical tasks before the results of the test are known. Additionally, the user must handle chemicals that are harmful and/or corrosive, with the added potential to stain various fabrics due to the dye nature of the testing compounds.

Another method commonly used to test the pH of a water sample involves use of indicator dyes deposited on test strips. According to these methods, a test strip is dipped into the water sample, allowing a color to develop. The color of the developed test strip is then compared to reference colors corresponding to known pH values, allowing identification of the pH of the water sample. This method is gaining popularity due to the convenience factor, but is limited due to an increased expense relative to the solution based methods. The test strips are not reusable or reversible, and the user must discard the test strip after using the product, thereby adding to the cost of this method. In addition, test strips rapidly degrade when left in aqueous solution and are not suitable for continuous monitoring of water chemistry.

Unfortunately, a product has not yet been described that allows continuous monitoring of an aquatic environment, is inexpensive and accurate, and is suitable for continuous pH monitoring and reuse in multiple applications. Thus, a need exists for reusable devices and methods for continuously monitoring the pH of an aquatic environment that are inexpensive and accurate, and that remove the requirement of the user to physically perform multiple mixing and measuring steps.

SUMMARY OF THE INVENTION

The present invention relates to devices and methods for quickly and easily measuring and monitoring the pH of a variety of aquatic environments including, without limitation, drinking water, well water, rivers, lakes, aquariums, pools, hot-tubs, and spas. The current invention includes devices that are reusable and capable of monitoring the pH in a reversible fashion, thereby allowing continuous pH sensing without a need for the user to physically perform pH tests. Operation of the invention involves placing the device into the aquatic environment and optically detecting a color change in the membrane, for example, by looking at the device when a pH measurement is desired. In addition, the device is both inexpensive and reusable, allowing the user to monitor the pH of various aquatic environments at minimal costs.

In one embodiment, the invention relates to a reusable device for continuously monitoring the pH of an aquatic environment. The device includes a sensor membrane, a support structure for mechanically supporting the sensor membrane, and a color reference chart. The sensor membrane includes a membrane and an indicator dye immobilized therein, where the indicator dye changes color corresponding to a pH of an aqueous solution contacted with the sensor membrane. The support structure is positioned such that at least one surface of the membrane is contacted with aqueous solution upon immersion of the device in an aquatic environment. In other embodiments, the support structure and sensor membrane can be positioned such that at least two surfaces of the sensor membrane are capable of being contacted with the aqueous solution. The color reference chart includes a chart displaying a plurality of colors, wherein each color corresponds to a reference pH value.

A membrane of the invention can be charged, such as positively charged or negatively charged, or neutral. A membrane is typically hydrophilic and can be a synthetic membrane, such as a polyamide membrane, or natural membrane, such as a cellulose membrane. In one embodiment, the membrane is a positively charged polyamide membrane.

A device of the invention can include various indicator dyes or mixtures thereof. For example, an indicator dye useful in a device of the invention can include bromophenol blue, congo red, methyl orange, resorcin blue, alizarin, methyl red, bromoceresol purple, chrophenol red, bromothymol blue, phenol red, neutral red, tumaric curcumin, or phenolphthalein. In one embodiment, the sensor membrane includes a mixture of bromothymol blue and phenol red.

A device of the invention can further include a structure for immersing the device in the aquatic environment. In one example, the structure for immersing includes an apparatus for affixing the device to a container.

In another embodiment, the invention includes a device for continuously monitoring the pH of an aquatic environment, including a sensor membrane designed to monitor pH of at least 6, and a support structure. Such a device includes a sensor membrane having a membrane and an indicator dye immobilized therein. The indicator dye immobilized to the membrane corresponds to the pH of an aqueous solution contacted with the sensor membrane and the indicator dye changes color at a pH of at least 6. The support structure mechanically supports the sensor membrane, and is positioned such that at least one surface of the membrane is contacted with aqueous solution upon immersion of the device in an aquatic environment. The device may optionally include a color reference chart displaying a plurality of colors, wherein each color corresponds to a reference pH value.

In another embodiment, the invention includes a method for detecting the pH of an aqueous solution. Such a method includes providing a reusable device having a sensor membrane including a membrane and an indicator dye immobilized therein, wherein the indicator dye changes color corresponding to a pH of an aqueous solution contacted with the sensor membrane; a support structure for mechanically supporting the sensor membrane, positioned such that at least one surface of the membrane is contacted with aqueous solution upon immersion of the device in an aquatic environment; and a color reference chart displaying a plurality of colors, wherein each color corresponds to a reference pH value. The method of the invention further includes contacting the sensor membrane with an aqueous solution of a first aqueous environment and optically comparing the membrane with a color reference chart, thereby detecting the pH of the aqueous solution of the first aqueous environment. In one embodiment, methods of the invention further include contacting the sensor membrane with an aqueous solution of a second aqueous environment and optically comparing the membrane with the color reference chart, thereby detecting the pH of the aqueous solution of a second aqueous environment.

The devices and methods of the invention can also be adapted, using fabrication techniques described herein, for monitoring other parameters of water chemistry, for example, by substituting pH indicator dyes with indicator dyes or other chemicals that change color in response to water chemistry parameters other than pH. Such parameters can include, for example, temperature, or concentrations of compounds such as ammonia, bromide, chloride, or nitrate, or other water chemistry parameters.

BRIEF DESCRIPTION OF THE DRAWINGS

FIG. 2 illustrates a side view (FIG. 2A) and a front view (FIG. 2B) of a device according to one embodiment of the invention.

DETAILED DESCRIPTION OF THE INVENTION

The present invention relates to a reusable device for continuously monitoring the pH of an aquatic environment. The device includes a mechanical support structure and a sensor membrane. A sensor membrane includes indicator dye immobilized to a membrane, such as a polyamide membrane. The device typically includes a color reference chart displaying multiple colors, where each color corresponds to a reference pH value. The device operates by having the sensor membrane submerged below water. The pH dyes immobilized to the sensor membrane change color in response to the pH value of the aquatic environment, thereby providing real-time, visual feedback in a reversible manner.

Figure 1:
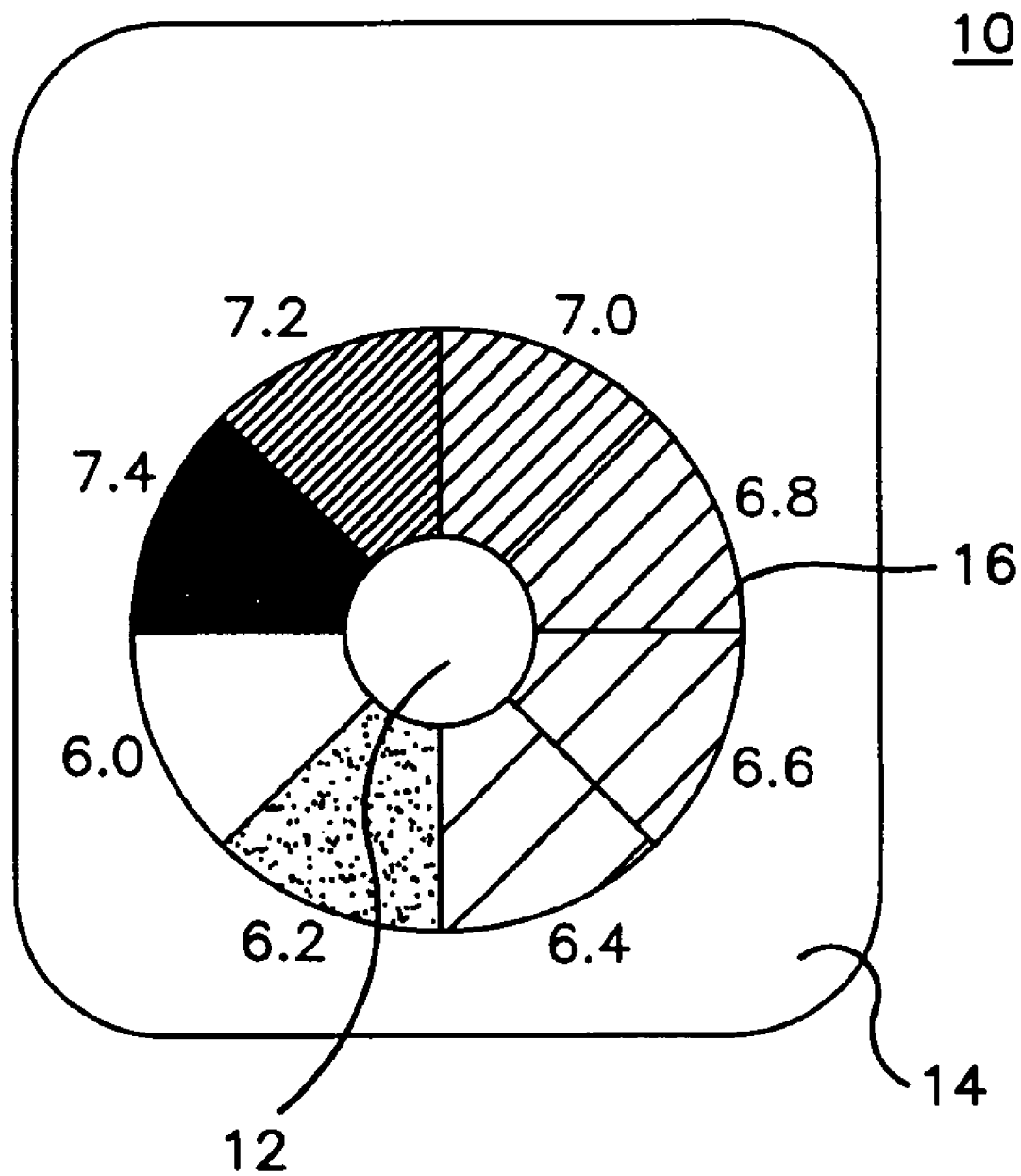
FIG. 1 shows a reusable device for continuously monitoring the pH of an aqueous environment, according to an embodiment of the invention (FIG. 1).

Devices of the invention are illustrated in FIG. 1 and in FIG. 2 (FIG. A-FIG. B). Referring to FIG. 1, one embodiment of a device 10 of the invention includes a sensor membrane 12, a support structure 14, and a color reference chart 16. The sensor membrane 12 includes a membrane having an indicator dye immobilized therein. The indicator dye changes color corresponding to the pH of an aqueous solution contacted with the sensor membrane 12. The support structure 14 is capable of mechanically supporting the sensor membrane 12. The support structure 14 and sensor membrane 12 are positioned such that at least one surface of the sensor membrane 12 is contacted with aqueous solution upon immersion of the device 10 in an aquatic environment. The color reference chart 16 includes a plurality of colors, wherein each color corresponds to a reference pH value. The pH values corresponding to the colors of the color reference chart may optionally be included on the device, as illustrated. The exemplary pH values 6.0, 6.2, 6.4, 6.6, 6.8, 7.0, 7.2, and 7.4 are illustrated in FIG. 1, although it will be recognized that the inventive device need not include those values as illustrated and/or may include pH values other than those exemplified in FIG. 1.

FIG. 2A-B illustrate an embodiment of the device 10 wherein the support structure includes a plurality of layers. The support structure includes a bottom support layer 18 and a top layer 20. The sensor membrane 12 can be positioned between the bottom and top layers 18, 20, and held in place by the joining of the top layer 20 and the bottom layer. One or more of the layers 18, 20 can include a cutaway access section such that the aqueous solution of an aquatic environment with which the device 10 is contacted can contact the sensor membrane 12. Such a access section is exemplified in FIG. 2A as access 22 in the bottom layer 18

Figure 3:
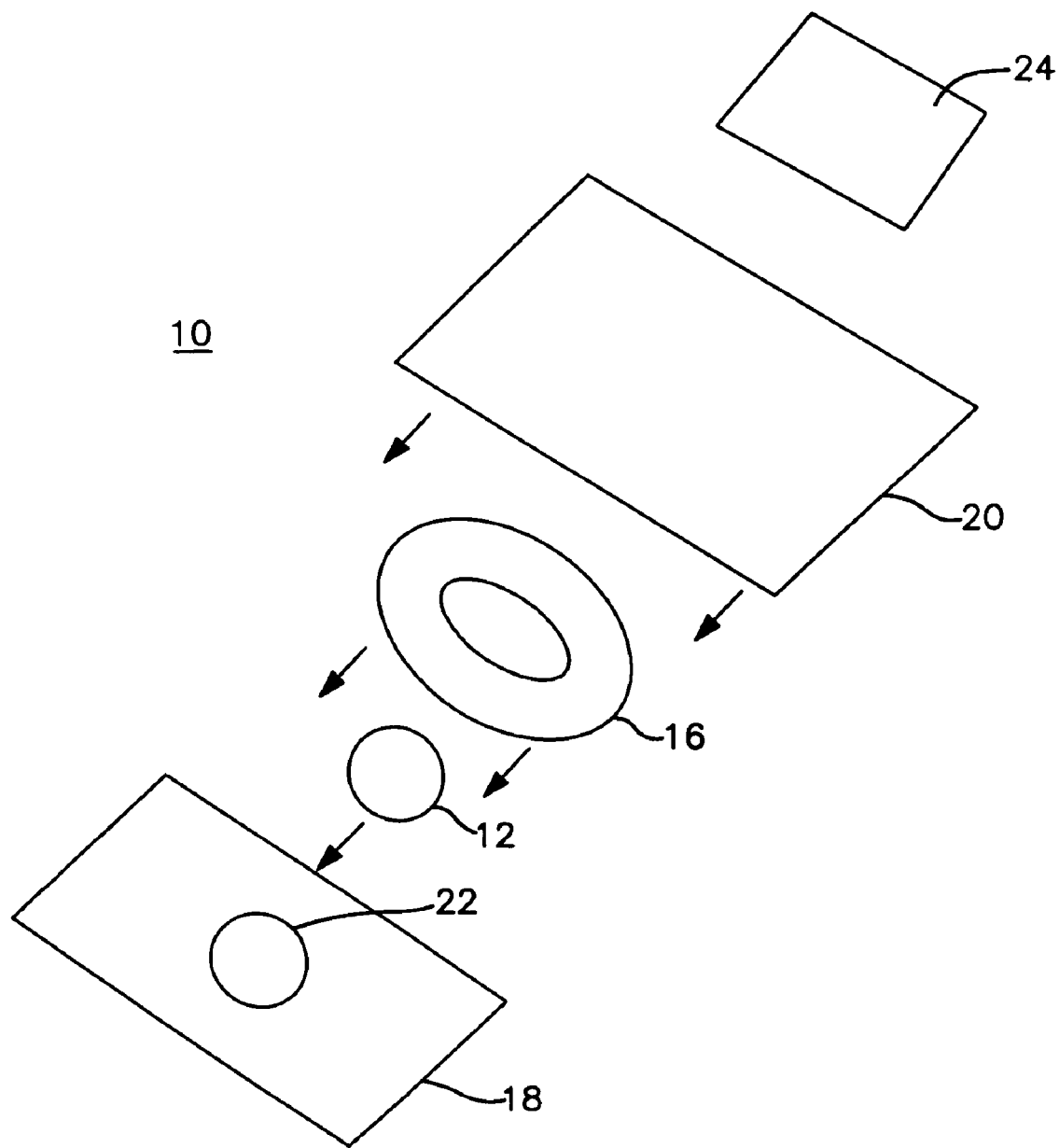
FIG. 3 shows an exploded view of a device according to an embodiment of the invention (FIG. 3).

FIG. 3 illustrates an exploded view of a device 10 of the invention. The device includes a bottom support layer 18 with an access 22 that allows direct contact with aqueous solution and at least one side of the sensor membrane 12. The device further includes a color reference chart 16 (colors not shown in illustration) and a top layer 20 for keeping the sensor membrane 12 in position. Although the color reference chart 16 and the top layer 20 are illustrated as separate, it will be recognized that in some embodiments, the color reference chart and the top layer can be embodied as one layer. Such an embodiment may include, for example, a color reference chart printed, screened or otherwise joined with a top layer that functions to keep the sensor membrane in a desired position. A device of the invention can optionally include a light-blocking element 24 that prevents at least a portion of the spectrum of light from reaching the sensor membrane 12. The light-blocking element 24 is illustrated in FIG. 3 as an individual and separate layer, but may alternatively be present, for example, as a component of the sensor membrane, such as a property of an indicator dye or of the membrane, or a light-blocking element may be include a property or component of a different layer of the device, such as the top layer 20.

A sensor membrane according to the present invention includes an indicator dye immobilized to the membrane. Various indicator dyes are known in the art including, for example, bromophenol blue, congo red, methyl orange, resorcin blue, alizarin, methyl red, bromoceresol purple, chrophenol red, bromothymol blue, phenol red, neutral red, tumaric curcumin, or phenolphthalein. A selection of various indicator dyes, as well as pH ranges at which they change color, will be apparent to those skilled in the art (see, for example, "Indicators", E. Bishop, Pergamon Press, 1972, chapter 3, which is incorporated herein by reference).

As used herein, the term "sensor membrane" refers to a membrane substrate having at least one indicator dye immobilized therein and capable of prolonged immersion in an aqueous solution without significant detectable dissociation of the dye from the membrane. A membrane or membrane substrate suitable for use in the current invention includes any substrate capable of having an indicator dye immobilized therein and suitable for use as a sensor membrane. A membrane can be a natural or synthetic substrate, and is typically hydrophilic. For example, synthetic substrates can include polyamide substrates such as various forms of nylon and nylon derivatives (e.g., Nylon 6.6), acrylamides, polyvinylidene fluoride, polypropylene, polyethersulfones, or polysulfones, or any ion exchange media. Alternatively, a suitable membrane substrate can include natural materials such as cellulose, cellulose derivatives, or nitrocellulose. A membrane can be charged, such as positively charged or negatively charged, or can be neutral. Whether a membrane is charged is determined with reference to the net balance of charges at the surface of the membrane at the pH range of interest. Various substrates suitable for use and membranes of the invention are commercially available and include, for example, Immobilon-Ny (uncharged) and Immobilon-Ny+ (positively charged nylon), both available from Millipore Corp., as well as Biodyne A (amphoteric surface, polyamide membranes), Biodyne B and Biodyne Plus (positively charged, polyamide membranes), Biodyne C (neutral or amphoteric, polyamide membranes), all available from PALL Gelman Laboratory or Amersham/GE Healthcare's Hybond N+ and Hybond XL series.

As used herein, the term "light blocking element" refers to an element of the device that is capable of blocking or preventing at least a portion of the visible or non-visible light spectrum. A light-blocking element may be desirable where an indicator dye of the sensor membrane is prone to degradation upon exposure to a portion of the light spectrum. A light-blocking element, therefore, functions to block a portion of the light spectrum, including a portion which may cause indicator dye degradation. Such a layer is typically at least partially transparent such that a user is able to view the sensor membrane, but capable of screening out at least a portion of the light spectrum (e.g., ultraviolet light). However, in some cases a light-blocking element is positioned on a side of the device not typically viewed by the user (e.g., back side or side opposite to a side having a color reference chart), in which case a light-blocking element need not be transparent, but can be opaque. A light-blocking element can be an individual layer of the device or can refer to a component or property of a portion or layer of the device. In one embodiment, a light-blocking element includes a layer or piece or material such as plastic positioned on one side of the device. In another embodiment, a light-blocking element can include a material (e.g., nylon, cellulose, or derivative thereof) positioned between layers of the device. Examples of such light-blocking elements include commercially available black or gridded nitrocellulose membranes, such as those sold by Millipore Corporation or Sterlitech Corporation. In another embodiment, a light-blocking element can include a dye (such as an indicator dye) or substance incorporated into the sensor membrane. Various other embodiments of a light-blocking element may be envisioned.

The device and methods of the invention are suitable for use in a variety of aquatic environments including, without limitation, bodies of fresh or salt water, lakes, rivers, etc., as well as drinking water or potentially potable water, wells, springs, etc. Aquatic environments can further include water maintained for recreation or bathing, such as pools, spas, baths, hot tubs, etc., as well as aquatic environments designed for containing aquatic life such as aquariums, fish tanks, fisheries, etc. Other aquatic environments amenable to use of water chemistry testing devices and methods as described herein may be apparent to the skilled artisan. As used herein, the term "aqueous solution" refers to any liquid solution derived from an aquatic environment in which detection of a water chemistry property (e.g., pH) is desired.

As used herein, the term "prolonged immersion" refers to the immersion of a sensor membrane in an aqueous solution for a period of time that is greater than the minimum time necessary to detect the pH of the aqueous solution with a device of the invention. Typically, the minimum time necessary for a device of the invention to be submersed in an aqueous solution in order to obtain a reading of the pH of the aqueous solution is about 20 seconds to one minute. According to the current invention, however, the devices are designed for monitoring the pH of an aquatic environment over a much longer time period. As such, sensor membranes of the invention are suitable for immersion and exposure to an aqueous solution for prolonged periods of time. The time of a prolonged immersion, however, depends in part on the purpose of the immersion. A prolonged immersion can be shorter where the purpose is to detect whether significant detectable dye dissociation occurs, as compared to where the purpose is to operate the device to continuously monitor the pH of an aqueous environment. For example, in one embodiment prolonged immersion can include 30 minutes to one hour, but can include 2, 4, 6, 10, 12, 18, 24, 36, 48, 72 hours. In other instances, prolonged immersion can include immersion in an aqueous solution for up to one week, or can include a period longer then a week, such as one month, six months, or one year.

The methods and device of the invention are suitable for continuous monitoring of an aquatic environment and may also be used as a reusable testing device that may dry out between applications and still function properly. Thus, in another example, prolonged immersion can include multiple and/or intermittent contacting with an aqueous solution or multiple different aqueous solutions. For example, a user may place the device in a single aquatic environment and leave it there such that it operates continuously and without interruption throughout the lifetime of the product or, alternatively, the user may opt to use the device to test multiple aquatic environments, such as by contacting the device with an aqueous solution from a first aquatic environment to test a water chemistry property and then contacting the device with an aquatic solution of a second aquatic environment to test a water chemistry property of the second aquatic environment. As such, the sensor membrane and device of the invention is said to be reusable in that it is suitable for continuous monitoring of an aqueous solution, including multiple uses with the same or different aqueous solution.

As used herein, the terms "significant dissociation", "detectable dissociation", or "significant detectable dissociation" of dye from a sensor membrane refer to bleeding of dye into aqueous solution, detectable by inspection with the naked eye, upon immersion of a sensor membrane in an aqueous solution. Significant dye dissociation can be detected, for example, by examining a device of the invention immersed in an aqueous solution at a pH range of interest and a predetermined temperature, for a given amount of time. For example, a device can be examined for significant detectable dissociation at a pH in the range of 6 to 9, and 10° C.-80° C. for 30 minutes to several weeks.

The term "pH range of interest", as used herein, refers to a range of pH at which examination of the pH of a given aqueous environment is desired and generally corresponds to the pH range at which the indicator dye of a given device changes color corresponding to the pH of an aqueous solution contacted with the sensor membrane. The pH range of interest is selected by a user of the device and typically corresponds with a property of an aquatic environment of which pH monitoring is desired. For example, a substantially neutral pH (e.g., pH 6-8) is typically desired in aquariums and pools in order to optimize the health conditions of the aquatic life or pool users, respectively. In other embodiments, a broader pH range of interest, such as 6-9, may be desired. Alternatively, pH range of interest may include any range desirable including, for example, highly acidic conditions (e.g., pH 1-3), moderately acidic (e.g., pH 3-4), slightly acidic (e.g., pH 4-6), slightly basic (e.g., pH 8-10), moderately basic (e.g., pH 10-11), or highly basic (e.g., pH 11-14).

The current invention additionally includes methods of fabricating a sensor membrane suitable for a device of the invention. The method generally includes selecting a membrane and a dye, and immobilizing the dye to the membrane. A variety of dyes and membranes are suitable for use in the current invention (see above), and a combination of membrane and dye is selected based, in part, on the ability of the dye to non-covalently bind to the membrane. An example of non-covalent binding includes immobilization of the dye to the membrane due to hydrogen bond or electrostatic interactions between the dye and the membrane. The ability of a membrane and a dye to form electrostatic interactions will be apparent to one skilled in the art, viewing the chemical structures of these sensor membrane components, particularly, the indicator dyes and functional groups of the membrane. Selection of a suitable membrane further includes comparing properties of a given membrane, such as the isoelectric point or pKa of functional groups of the membrane, with a given pH range of interest. For example, where a given membrane is a positively charged membrane, it is desirable that the isoelectric point of the membrane not be below the pH range of interest. In certain embodiments, the isoelectric point of a positively charged membrane used as a sensor membrane is above the pH range of interest.

Following selection of an indicator dye (or mixture of dyes) and a membrane, the indicator dye is immobilized to the membrane. For example, the dyes are immobilized on the membrane with a procedure that constitutes soaking the membranes in a dilute aqueous solution of indicator dye for a period sufficient to allow the indicator dye to diffuse into the membrane (indicator dye soaking step). Soaking typically includes a time period of at least 30 minutes, but in some instances 8, 10 or 12 hours, and sometimes 16 or 20 hours, or greater than 24 hours, depending on the membrane and the indicator dyes used, including the rate of uptake of the dye by the membrane and how evenly distributed upon the membrane surface the dye is at the allotted soaking time. The membranes are then rinsed with a solution, such as neutral water, until no more dye is easily rinsed/washed away. A sufficient allotted time of soaking a membrane in a solution of indicator dye will be visually apparent where the membrane retains indicator dye evenly distributed therein after the steps of soaking and rinsing. Following rinsing/washing, the membranes are soaked in solutions of either water adjusted to pH values just above and below the upper and lower limits listed as the working ranges or pH range of interest for the particular pH dyes (for example, membranes can be soaked with pH=10.0 and 5.0 buffer for a working range of 6.0-9.0) or buffer solutions with similar pH ranges. Soaking is continued until there is no significant dissociation of indicator dye into the water or buffered solution. The membranes are typically soaked for a period of at least 2 minutes to about 30 minutes, but in some cases can be several hours to about 24 hours. The membranes are rinsed with solution, such as neutral water, at least one additional time and allowed to dry for a period of at least 1 hour in air.

A device of the invention further includes a support structure for mechanically supporting the sensor membrane. The support structure is coupled with the sensor membrane, and the support structure and sensor membrane are positioned such that at least one surface of the membrane is contacted with aqueous solution upon immersion of the device in an aquatic environment. Various embodiments of a support structure are intended to be within the scope of the invention. For example, the support structure can be a solid material, such as a metal, glass, plastic, composite or any other material capable of mechanically supporting a sensor membrane in an aqueous environment. The support structure can be a single, continuous piece of material, or can be an assembly of multiple pieces. For example, the support structure may include two pieces that are capable of being joined together, such as by screw, snap, latch or any other known means for joining two pieces, wherein a sensor membrane is positioned between the two pieces to form a "sandwich". In another example, two pieces may be joined by a hinge, as to form a single piece, hinged support structure that folds onto a sensor membrane. In such embodiments, a portion of at least one side of the sensor membrane would be exposed to aqueous solution upon immersion therein. In one embodiment, the sensor membrane can be coupled to a plastic support using a small cutaway in the plastic and then placing another piece of plastic on top of the small hole so as to physically hold the membrane in place. The membrane is then open to the aquatic environment from both directions, allowing maximum lateral water flow through the membrane (see FIGS. 1 to 3).

A device of the invention can further include a color reference chart. Such a chart displays a plurality of colors, where each color corresponds to a reference pH value. Reference pH values and corresponding colors present on a color reference chart of a given invention will be selected based on the indicator dyes immobilized to the sensor membrane of the device. Appropriate colors corresponding to reference pH's, matched with the dyes of a device will be apparent to those skilled in the art. For example, where the sensor membrane consists of bromothymol blue alone, a color reference chart will include various shades of yellow and blue, each color corresponding to a pH in the range of about 6.0-8.6. In another embodiment, where the sensor membrane consists of a mixture of bromothymol blue and phenol red, a color reference chart can include, for example, yellow corresponding to a pH value of about 6.2, very light green corresponding to a pH value of about 7.0, green corresponding to a pH value of about 7.6, blue-green corresponding to a pH value of about 8.), and blue corresponding to a pH value of about 8.6 and above. One skilled in the art will recognize that gradual color shades between those specifically identified correspond to pH values between the associated and indicated pH values. A color reference chart is positioned such that the color of sensor membrane is quickly and easily compared to a reference color, in order to determine the pH of the aqueous solution. The chart should be easily visible in order for the user to compare the color of the sensing layer with the colors on the reference chart and the activity required by the user for making such a comparison should be limited to directing the user's attention in the direction of the device. Typically, but not necessarily, a color reference chart is present directly on the device. For example, a color reference chart may be positioned on the device and adjacent or nearby the sensor membrane. In another embodiment, the color reference chart can be positioned separate from the device, but near the location of the device such that a comparison can be made by directing the user's attention to the general area (within a meter) of the sensor membrane.

The device can further include a structure for immersing the device in the aquatic environment. Such a structure can include a weighted body, such as a piece of metal, attached to the device to prevent the device from floating to the surface of aquatic environment. In some embodiments, the support structure is sufficient to keep the device immersed in the aquatic environment, thereby obviating the necessity of an additional structure for immersing the device. In another embodiment, a structure for immersing is coupled with the device such that the device floats freely near the surface of the aquatic environment, thereby allowing the user to visually locate and inspect the sensor membrane of the device without having to remove it from the aquatic environment, but while maintaining the sensor membrane immersed in the aquatic environment. In another embodiment, the structure for immersing the device includes an apparatus of affixing the device to the aquatic environment container in such a manner that the pH sensitive membrane is submerged beneath the surface of the water. Such an apparatus may include suction cups, a bio-compatible and water resistant adhesive, flotation device that holds the surface of the pH sensitive membrane beneath water, a clip that attaches to a wall, side, or bank of the aquatic environment container, or a hook that also attaches to a wall of the container, but may be moved laterally without applying pressure as would be required for the clip. Various other immersion structures, including additional apparatus for affixing the device to the aquatic environment container, will be known or recognized by those skilled in the art.

The devices and methods of the invention can also be adapted, using fabrication techniques described herein, for monitoring other parameters of water chemistry. For example, pH indicator dyes can be substituted with indicator dyes or other chemicals that change color in response to water chemistry parameters other than pH. Such parameters can include, for example, temperature, or concentrations of compounds such as ammonia, bromide, chloride, or nitrate. Other water chemistry parameters will be apparent to those skilled in the art.

The following examples are intended to illustrate but not limit the invention.

EXAMPLE 1

Fabrication of pH Indicator Device

This example illustrates a device and method of measuring the pH of aquatic environments, such as aquariums, pools, hot-tubs, etc. The method involves a device capable of monitoring the pH in a reversible fashion creating the opportunity for continuous pH sensing, removing the requirement of the user to physically perform pH tests. Operation of the invention involves placing the device into the aquatic environment, and optically detecting a color change in the membrane, for example, by looking at the device, when a pH measurement is desired.

The method of testing pH as described herein utilizes a device that is designed to be reversible or reusable and is capable of continuously monitoring the pH value. The device contains an active layer or sensor layer (i.e., sensor membrane) in which a pH sensitive dye (see Table 1 for example dyes and associated pH ranges) is immobilized such that the dye does not bleed out into the aquatic environment. In addition, the device contains a color reference chart containing colors that correspond to specified pH values, providing a means to read the pH sensitive layer without additional steps or reference materials (see, for example, FIG. 2). The invention includes a means for immersing the device in an aquatic environment, such as by affixing the device to the walls of the aquatic container in any desired location. In one example, can be accomplished with the inclusion of an appropriate amount of suction cups. The appropriate amount will depend on the size of the device and the application. For example, larger devices required for swimming pools than for small aquariums. Other examples of structures for immersing the device in an aquatic environment can include a temporary waterproof glue, a clip that attaches to the container walls, or a hook that rests on the top of the container holding the pH sensitive material beneath the surface of the water. The pH sensitive layer is mounted on a plastic material that supports the entire device, including the sensing layer, color reference chart, and suction cups or glue backing.

TABLE 1

| Dye | Active pH Range |
| --- | --- |
| Bromophenol Blue | 2.0-4.6 |
| Congo Red | 3.0-5.0 |
| Methyl Orange | 3.2-4.4 |
| Resorcin Blue | 4.4-6.2 |
| Alzarin Red S | 4.6-6.0 |
| Methyl Red | 4.8-6.0 |
| Bromoceresol Purple | 5.2-6.8 |
| Chrophenol Red | 5.2-6.9 |
| Bromothymol Blue | 6.0-7.6 |
| Phenol Red | 6.6-8.0 |
| Neutral Red | 6.8-8.0 |
| Tumaric Curcumin | 7.4-8.6 |
| Phenolphthalein | 8.2-10.0 |

The sensor membrane or pH sensing layer is the active component in the invention and provides the real-time pH value. The layer includes a pH indicator dye, such as those selected from the list above. Appropriate dyes are selected based on the pH range intended for monitoring, as each dye has a specific pH range in which color changes occur (see Table 1). The active range of the pH dye while immobilized onto a sensor membrane may be discovered after immobilization is carried out and color calibration at various pH values is accomplished. Typical active pH ranges may differ slightly in immobilized form from a pure solution test. Additionally, the membrane of a sensor membrane, typically a hydrophilic membrane, is the layer within which the dye is immobilized. The membrane can be hydrophilic to allow water access through the pores so that the pH dyes immobilized thereto will provide real-time measurement of the pH values. The membrane may be constructed from nylon derivatives, or cellulose derivatives, including mixed ester nitrocellulose. Membranes that have been functionalized with positively charged species such as Millipore Corporation's Immobilon-Ny and Immobilon-Ny+, and Pall Corporation's Biodyne B and Biodyne Plus or Amersham's Hybond N+ and Hybond XL membranes are well suited for immobilizing pH dyes (either the sodium salt or pure compound), which is often commercially available from numerous chemical providers.

Without being bound by any one particular theory, the immobilization of a pH dye onto a membrane can possibly be a function of the hydrogen bond interactions between the dye and the membrane, in addition to the electrostatic interaction of the charged particles. For example, nylon includes both hydrogen bond donors (N—H bonds of the amide linkage comprising the backbone of nylon) and hydrogen bond acceptors (C=O, and N—H bonds of the amide functionality), potentially leading to multiple hydrogen bonding interactions between the dye and substrate (see chemical structure of nylon, listed below). However, each amide linkage is separated by a specified number of methylene units ($CH_2$, the number of which is used to determine the nylon specification, i.e., six $CH_2$ units for nylon 6, 6') and therefore there is a significant amount of molecular space occupied by non-hydrogen bonding interactions. The hydrogen bonding capacity of this compound is determined by the number of hydrogen bond donors and acceptors relative to non-hydrogen bonding units. For nylon, there are 2 non-hydrogen bonding units for every hydrogen bond donor or acceptor. Nylon's capacity for immobilizing pH dyes is determined, in large part, by this ratio.

Where the membrane selected for use as a sensor membrane is a positively charged membrane, the presence of the positive charges at the pH range of interest enables optimum dye immobilization. In such a case, a membrane with a high isoelectric point (pH value at which there are equal positive and negative charges) would create a situation in which positive charges would be present on the surface of the membrane even at high pH values. This property creates the potential to keep the dyes both hydrogen bound and most importantly electrostatically bound to the surface of the membrane. If, however, the isoelectric point is below the pH range of interest the positive charges will be significantly reduced at higher pH values due to the increasing basicity of the solution, resulting in loss of electrostatic interaction of the dye with the membrane. As a result, the dye will leak out into solution at high pH values. For this reason, where the membrane is a positively charged membrane, it is important that the isoelectric point be at the higher end of the pH range of interest for measurement.

The dyes are chosen for example, from the list above (Table 1), to suit the intended range of pH values that will be monitored. In many cases, a mixture of pH dyes is typically required to provide a full range of values that will be monitored with the device. In the current example, the dyes bromothymol blue and phenol red were immobilized to several positively charged polyamide membranes (e.g., Immobilon-Ny+, Biodyne B and Biodyne Plus). To achieve the full range needed for routine sensing in aquatic environments as exemplified in aquariums, pools, and hot-tubs, a 1:1 mixture of bromothymol blue and phenol red were immobilized to provide the 6.0-9.0 range desired for pH testing. In instances in which a broader range of pH values is needed, appropriate dyes would be immobilized to accommodate the necessary pH range.

Fabrication of the Sensor Membrane

A typical fabrication of the color coded real-time pH sensing device involves the initial preparation of a dilute (mM or less) aqueous solution of the pH dyes (for example, those dyes selected from Table 1) based on their specified use. For example, the following range of concentrations of the dyes bromothymol blue and phenol red were determined appropriate: $1\times10^{-4}$-$1\times10^{-6}$ M. The hydrophilic membranes are typically soaked in the solution for a period of time at least 30 minutes, preferably with constant stirring or rocking motions to ensure complete coverage of the membranes. The membranes are then rinsed with a generous amount of neutral water, followed by soaks in buffered solutions of several pH values ranging from just below the lower limit for the pH dye, to just above the upper limit, for a rinsing period of at least 2 minutes. For example, using bromothymol blue, buffers with pH values of 5.0 and 9.5 were suitable in addition to several buffers in between those values. The membranes are then rinsed one final time with neutral water and allowed to dry in air for a period of at least about 1 hour. The mounting of the membrane onto the solid support can be carried out by placing the membrane in the designated cutaway on the plastic support, and then covering with the second plastic layer having the graphical illustration of the color reference chart.

Fabrication of a reusable device of the invention is exemplified as set forth below. First, a ½ inch (12.7 mm) or 13 mm diameter membrane circles were cut out and 2.0 g weighed out (approximately 200 membrane discs). An opaque maroon solution of indicator dyes was prepared by mixing 0.125 g (0.19 mmol) bromothymol blue sodium salt (3'-3"-Dibromothymolsulfon-phthalein; CAS: 34722-90-2; $C_{27}H_{27}Br_2NaO_5S$; Molecular Weight: 646.38; obtained from Alfa Aesar) and 0.055 g (0.15 mmol) phenol red sodium salt (Phenolsulfonphthalein; CAS: 34487-61-1; $C_{19}H_{13}NaO_5S$; Molecular Weight: 376.36; obtained from TCI America), both dissolved in 400 mL water (1.27/1 molar ratio of bromothymol blue/phenol red). The opaque maroon solution is shaken with 200 membranes overnight (approximately 18-24 hrs.) and then rinsed with tap water to remove excess dye not immobilized on membrane. Membranes were rinsed with 50 mL water adjusted to pH=1.8 (using concentrated HCl) for approximately 3-5 minutes. Membranes were then rinsed with 50 mL water adjusted to pH=12.5 (concentrated NaOH solution) five times, rinsing with tap water in between each basic treatment. The membranes were rinsed with pH=1.8 water one more time, then pH=12.5 water overnight (approximately 18-24 hrs.). Membranes were further washed with basic solution 4 times, once with the acidic solution, neutralized with tap water until all membranes are green, and then dried in air for several hours. Membranes are stored in sealed ziplock bags in the absence of light. Careful handling of membranes is recommended, and nitrile gloves are utilized to handle raw and dyed membranes. Once dry, membranes are ready for assembly.

Device Assembly

One circular membrane was cut in such a way that a small crescent shape was removed from the disc, resulting in a half-moon shape membrane. The sensor membrane (full circle) was attached to the adhesive side of the color reference wheel label by simply pressing the membrane to the label. The crescent shaped membrane was then placed into the recess into the plastic base and the adhesive backed label was applied to the plastic piece, making sure that the crescent shaped membrane remains in place within the recess of the plastic base. The adhesive was then flattened out by applying pressure to the face of the device in an even fashion. The suction cup, utilized as means of securing the device to a wall of a container, was then placed inside the hole on the top of the device to complete assembly.

EXAMPLE 2

Use of pH Indicator Device

The sensor membrane device of the invention allows accurate and convenient water chemistry testing (e.g., pH) on a regular basis. The device is suitable for use as a continuous pH monitor, but may also be used as a reusable testing device that may dry out between applications and still function properly. Device fabrication includes immobilizing colorimetric pH dyes on solid supports so that no dye leaks out into solution and the aquatic environment contacts the surface of the solid support creating an interaction between the colorimetric pH dye and the water. The dye adjusts appropriately to the pH of the solution and provides an accurate reading of the pH upon comparison of a reference color chart calibrated with standard buffer solutions. The lifetime of the device ranges from several weeks to several months, though the useful life of the device is dependent upon environmental conditions. It is estimated that the lifetime of a device of the invention can reach or even exceed six months of continuous use. Sensor membranes have been observed to retain function even upon immersion in water for an excess of 4 months in calibrated buffer solutions in small 10 mL vials. Active membranes have also been observed in real-world aquarium conditions for 2 months. Although some noticeable fading in intensity of the dye immobilized in the membrane does occur, the dye continues to undergo substantial color changing activity corresponding to changes in the pH of the aquatic environment, thereby indicating that the device retains functionality following this prolonged use.

TABLE 2

|  | Sensor Membrane Device | EMD Strips | Tetra Sol. | Aq Pharm. Sol. | Health Treas. Low Ion Sol. |
| --- | --- | --- | --- | --- | --- |
| Freehold, NJ | 0.84 | −0.18 | 0.82 | 0.62 | −0.19 |
| Staten Is. NY | 0.62 | −0.67 | 0.63 | 0.43 | −0.59 |
| Chicago, IL | 0.50 | 0.72 | 0.68 | 0.92 | 0.60 |
| Austin, TX | 0.59 | 0.73 | 0.82 | 0.92 | 0.73 |
| Columbia, MD | 0.54 | 0.34 | 0.89 | 0.79 | −0.12 |
| Scottsdale, AZ | 0.95 | 0.87 | 0.97 | 0.77 | 0.79 |
| Georgia | 0.73 | −0.51 | 0.49 | 0.29 | 0.04 |
| Mtn. View, CA | 0.85 | 0.89 | 0.89 | 0.99 | 0.67 |
| Tarpan Springs, FL | 0.86 | 0.84 | 0.85 | 0.80 | 0.35 |
| Howell, MI | 0.77 | 0.63 | 0.80 | 0.80 | −0.15 |
| Carmel, CA | 0.91 | 0.84 | 0.95 | 0.92 | 0.37 |
| Orlando, FL | 0.37 | 0.64 | 0.93 | 0.90 | 0.42 |
| Average Accuracy | 0.70 | 0.27 | 0.77 | 0.72 | 0.24 |

Table 2 lists the results obtained from comparison tests intended to measure and compare the accuracy of the sensor membrane device of the invention with that of existing methods of testing pH. The sensor membrane device was compared with EMD Science ColorpHast™ pH Indicator strips ("EMD Strips")(5-10 pH, obtained from Fisher Scientific, Inc.); Tetratest™ pH Freshwater Kit ("Tetra Sol.") (obtained from Tetra Werke); Aquarium Pharmaceuticals Freshwater Master Test Kit-Freshwater pH and High Range pH solutions as needed ("Aq. Pharm. Sol."); and Hydion pH Paper-Lo-Buff Lo Ion Test Kit ("Health Treas. Low Ion Sol.") (obtained from Health Treasures). The water samples used were obtained from numerous water sources across the continental United States in an effort to best understand the broad applicability of the sensor membrane device.

The accuracy readings are referenced to measurements from an electronic pH meter Mettler Toledo Portable pH/Ion Meter model MP120 pH (obtained from VWR International) operating in the "pH" mode, calibrated with standard pH=7.00 and 4.01 buffer sachets provided with the instrument. Additional calibration was carried out using Orion Color-Coded Buffers from Thermo Electron (7.00 and 4.01 pH values traceable to NIST Standard Reference Materials, obtained from Fisher Scientific). The accuracy reading itself is equal to the following formula:

$$\text{Accuracy} = 1 - \text{AVERAGE}(|R - T|)$$

Where R=reference pH measurement (electronic pH meter) and T=test pH measurement (sensor membrane device, test strips, solution, etc.)

The accuracy measurements indicate that a value closest to a numerical value of "1" indicates perfectly accurate, whereas lower values indicate increasingly inaccurate pH measurements. The results are listed in Table 2. It was observed that the accuracy of the sensor membrane device tended to increase with carbonate hardness. These results indicate that the sensor membrane device is substantially more accurate than the test strips and is comparable in accuracy to the solution-based method. One outlying value was removed for a more accurate comparison of the relative accuracies of the various methods. The exact reason for one anomalous value is unknown, but may have been related to the extremely low carbonate hardness of the sample.

Figure 4:
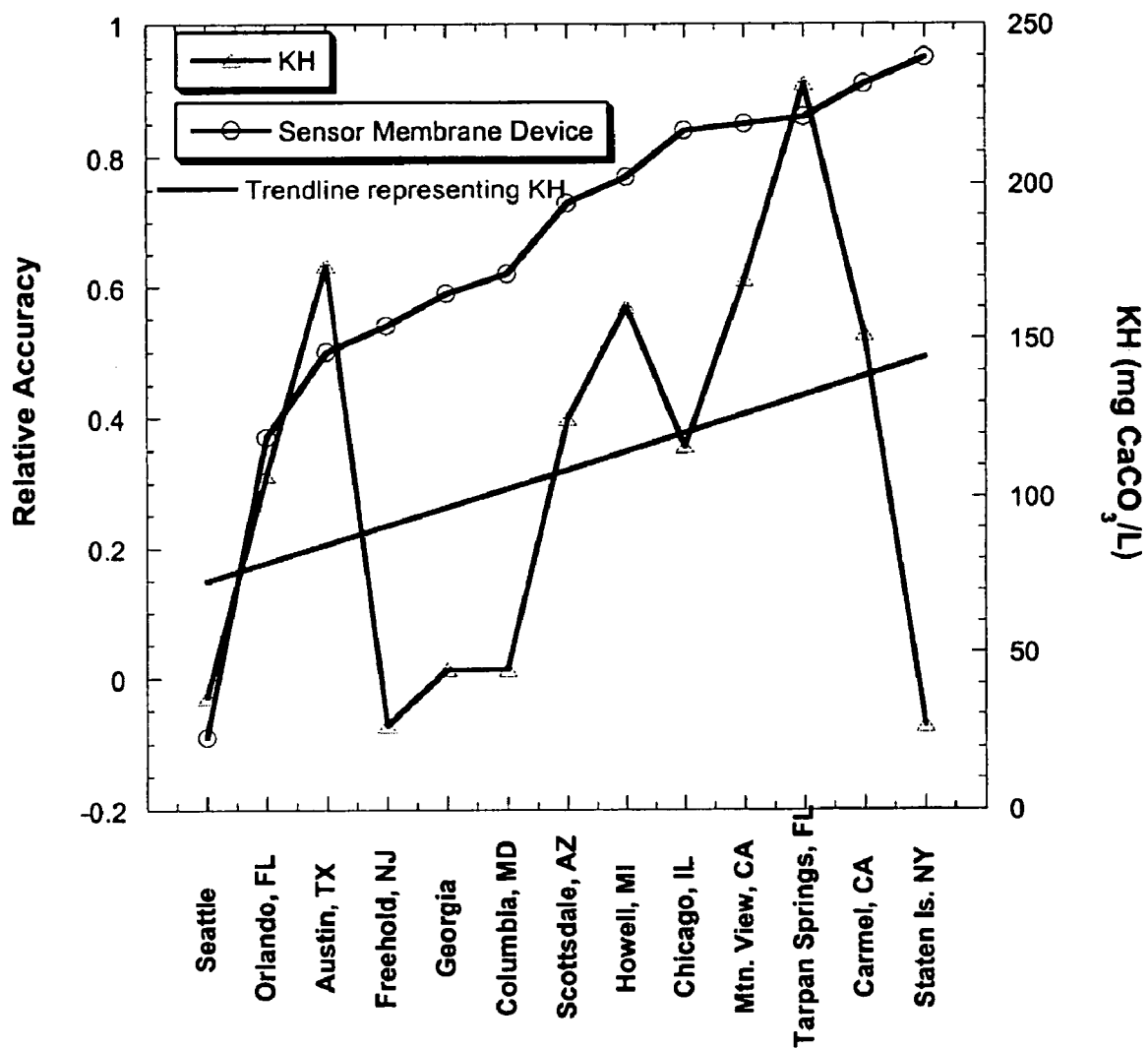
FIG. 4 illustrates pH measurements, obtained using the inventive device, in relation to carbonate hardness of various aqueous solution samples (FIG. 4).

In an effort to examine whether the sensor membrane device has improved accuracy in some water samples as compared to others, we have tested the water for various chemical components and found the following trend illustrated in FIG. 4. The plot illustrates the relationship between accuracy of the sensor membrane device and KH (carbonate hardness given in mg $CaCO_3/L$). A line is included as a linear fit of the KH data to indicate that the trend of the data is generally to increase from low accuracy to high accuracy, resulting in a positive relationship between accuracy of the sensor membrane device and KH (i.e., higher KH values lead to more accuracy in readings). There are some exceptions to the trend, but with a small sample size, the trend appears to be a real feature. It is known that low ion solutions, in general, often result in inaccurate pH measurements and accordingly there are specific products intended to address these particular cases including, for example, Hydrion pH Paper-Lo-Buff Lo Ion Test Kit (obtained from Health Treasures). From the data, however, it is apparent that the sensor membrane device of the invention is equally accurate or more accurate as compared to currently available technology regarding low ion solutions.

REFERENCES

Each of the following references is incorporated herein by reference.

Lowry, R. W. Pool Chlorination Facts; Lowry Consulting Group: Jasper, Ga., 2003.

Sanderfoot, A. E. What Color is Your Swimming Pool?; 3rd ed.; Storey Publishing, LLC: North Adams, Mass., 2003.

Tamminen, T. The Ultimate Pool Maintenance Manual; 2nd ed.; McGraw-Hill: New York, 2001.

Brady, J. E.; Holum, J. R. In Chemistry: The Study of Matter and Its Changes; John Wiley & Sons, Inc.: New York, 1996; pp 679-725.

Although the invention has been described with reference to the above example, it will be understood that modifications and variations are encompassed within the spirit and scope of the invention. Accordingly, the invention is limited only by the following claims.

What is claimed is:

1. A reusable device for continuously monitoring the pH of an aquatic environment, the device comprising:
   a) a reusuable sensor membrane comprising a polyamide membrane and an indicator dye immobilized therein, wherein the indicator dye changes color corresponding to a pH of an aqueous solution contacted with the sensor membrane;
   b) a support structure for mechanically supporting the sensor membrane, positioned such that at least one surface of the membrane is contacted with aqueous solution upon immersion of the device in an aquatic environment; and
   c) a color reference chart displaying a plurality of colors, wherein each color corresponds to a reference pH value.

2. The device of claim 1, wherein the polyamide membrane is a positively charged membrane.

3. The device of claim 1, wherein the polyamide membrane is a negatively charged membrane.

4. The device of claim 1, wherein the polyamide membrane is a neutral membrane.

5. The device of claim 1, wherein the indicator dye comprises bromophenol blue, congo red, methyl orange, resorcin blue, alizarin, methyl red, bromoceresol purple, chrophenol red, bromothymol blue, phenol red, litmus, neutral red, tumaric curcumin, or phenolphthalein.

6. The device of claim 1, wherein the indicator dye comprises a mixture of bromothymol blue and phenol red.

7. The device of claim 1, wherein the indicator dye changes color at a pH of less then 6.

8. The device of claim 1, wherein the indicator dye changes color at a pH of at least 6.

9. The device of claim 1, wherein the indicator dye changes color at a pH between about 6 and about 9.

10. The device of claim 1, further comprising a structure for immersing the device in the aquatic environment.

11. The device of claim 10, wherein the structure for immersing comprises a means for affixing the device to a container.

12. The device of claim 1, wherein the support structure and sensor membrane are positioned such that at least two surfaces of the sensor membrane are capable of being contacted with the aqueous solution.

13. The device of claim 1, wherein the aquatic environment comprises an aquarium, pool, hot-tub, or spa.

14. The device of claim 1, further comprising a light blocking element for blocking light from an external source.

15. The device of claim 1, wherein the color reference chart is optically comparable to the color change of the sensor membrane upon immersion of both the sensor membrane and the color reference chart in the aqueous solution for which pH is being monitored.

16. The device of claim 1, wherein the indicator dye is immobilized to the polyamide membrane by:
   (i) soaking the polyamide membrane in an aqueous solution of indicator dye for a period sufficient to allow the indicator dye to diffuse into the polyamide membrane,
   (ii) removing the polyamide membrane from the aqueous solution, and
   (iii) soaking the polyamide membrane in a wash solution having a pH value greater then 1.0 units above the upper limit of the pH range of the indicator dye and/or greater then 1.0 units below the lower limit of the pH range of the indicator dye until there is substantially no dissociation of indicator dye into the wash solution.

17. A reusable device for continuously monitoring the pH of an aquatic environment, the device comprising:
   a) a reusuable sensor membrane comprising a polyamide membrane and an indicator dye immobilized therein, wherein the indicator dye changes color at a pH of at least 6 and the indicator dye color corresponds to a pH of an aqueous solution contacted with the sensor membrane;
   b) a support structure for mechanically supporting the sensor membrane, positioned such that at least one surface of the membrane is contacted with aqueous solution upon immersion of the device in an aquatic environment; and
   c) a light blocking element.

18. The device of claim 17, wherein the polyamide membrane is selected from the group consisting of a positively charged membrane, a negatively charged membrane, or a neutral membrane.

19. The device of claim 17, wherein the indicator dye is bromophenol blue.

20. The device of claim 17, wherein the indicator dye is phenol red.

21. The device of claim 17, wherein the indicator dye changes color at a pH between about 6 and about 9.

22. The device of claim 17, further comprising a color reference chart displaying a plurality of colors, wherein each color corresponds to a reference pH value.

23. The device of claim 17, further comprising a structure for immersing the device in the aquatic environment.

24. The device of claim 23, wherein the structure for immersing comprises an apparatus for affixing the device to a container.

25. The device of claim 17, wherein the support structure and sensor membrane are positioned such that at least two surfaces of the sensor membrane are capable of being contacted with the aqueous solution.

26. The device of claim 17, wherein the aquatic environment comprises an aquarium, pool, hot-tub, or spa.

27. A method for detecting the pH of an aqueous solution, comprising:
   a) providing a reusable device, comprising:
      a sensor membrane comprising a polyamide membrane and an indicator dye immobilized therein, wherein the indicator dye changes color corresponding to a pH of an aqueous solution contacted with the sensor membrane;
      a support structure for mechanically supporting the sensor membrane, positioned such that at least one surface of the membrane is contacted with aqueous solution upon immersion of the device in an aquatic environment; and
      a color reference chart displaying a plurality of colors, wherein each color corresponds to a reference pH value;
   b) contacting the sensor membrane with an aqueous solution of a first aqueous environment; and
   c) optically comparing the membrane with a color reference chart, thereby detecting the pH of the aqueous solution of the first aqueous environment.

28. The method of claim 27, wherein the polyamide membrane is selected from the group consisting of a positively charged membrane, a negatively charged membrane, or a neutral membrane.

29. The method of claim 27, wherein the indicator dye comprises bromophenol blue, congo red, methyl orange, resorcin blue, alizarin, methyl red, bromoceresol purple, chrophenol red, bromothymol blue, phenol red, litmus, neutral red, tumaric curcumin, or phenolphthalein.

30. The method of claim 27, wherein the indicator dye changes color at a pH of less then 6.

31. The method of claim 27, wherein the indicator dye changes color at a pH of at least 6.

32. The method of claim 27, wherein the indicator dye changes color at a pH between about 6 and about 9.

33. The method of claim 27, wherein the first aquatic environment comprises an aquarium, pool, hot-tub, or spa.

34. The method of claim 27, wherein the device is continuously contacted with the aqueous solution for less them 30 minutes.

35. The method of claim 27, wherein the device is continuously contacted with the aqueous solution for at least one hour.

36. The method of claim 27, wherein the device is continuously contacted with the aqueous solution for at least 12 hours.

37. The method of claim 27, further comprising contacting the sensor membrane with an aqueous solution of a second aqueous environment and optically comparing the membrane with the color reference chart, thereby detecting the pH of the aqueous solution of a second aqueous environment.

38. The method of claim 27, further comprising the step of immersing the sensor membrane and the color reference chart in the first aqueous environment upon contacting the sensor membrane with the aqueous solution.

* * * * *